(12) United States Patent
Takashima et al.

(10) Patent No.: US 8,088,429 B2
(45) Date of Patent: *Jan. 3, 2012

(54) PACKAGE DRINK

(75) Inventors: Shinichiro Takashima, Tokyo (JP);
Masaki Iwasaki, Tokyo (JP); Kojirou Hashizume, Haga-gun (JP); Naoki Hosoya, Tokyo (JP); Shinji Yamamoto, Tokyo (JP); Yoshikazu Ogura, Tokyo (JP); Jun Saito, Kamisu (JP); Hitoshi Takaya, Kamisu (JP); Masami Shimizu, Tokyo (JP); Norihiko Satake, Tokyo (JP); Eiichi Hoshino, Tokyo (JP); Yukiteru Sugiyama, Tokyo (JP)

(73) Assignee: Kao Corporation, Tokyo (JP)

( * ) Notice: Subject to any disclaimer, the term of this patent is extended or adjusted under 35 U.S.C. 154(b) by 1066 days.

This patent is subject to a terminal disclaimer.

(21) Appl. No.: 10/581,200

(22) PCT Filed: Dec. 1, 2004

(86) PCT No.: PCT/JP2004/017875

§ 371 (c)(1),
(2), (4) Date: Jun. 1, 2006

(87) PCT Pub. No.: WO2005/053415

PCT Pub. Date: Jun. 16, 2005

(65) Prior Publication Data

US 2007/0128327 A1   Jun. 7, 2007

(30) Foreign Application Priority Data

| Dec. 2, 2003 | (JP) | 2003-402533 |
| Dec. 22, 2003 | (JP) | 2003-424557 |
| Feb. 26, 2004 | (JP) | 2004-050719 |
| Oct. 29, 2004 | (JP) | 2004-316760 |

(51) Int. Cl.
*A23F 3/16* (2006.01)
*A23L 2/72* (2006.01)
*A23L 2/80* (2006.01)
*C12H 1/02* (2006.01)

(52) U.S. Cl. ........ 426/597; 426/425; 426/431; 426/435; 426/423; 426/422

(58) Field of Classification Search ............... 426/422, 426/423, 424, 425, 428, 429, 435, 597, 590, 426/478, 479, 481, 487

See application file for complete search history.

(56) References Cited

U.S. PATENT DOCUMENTS

| 4,026,795 A | * | 5/1977 | Okamoto et al. | 502/33 |
| 4,229,612 A | * | 10/1980 | Hall et al. | 585/823 |
| 4,248,789 A | * | 2/1981 | Okada | 549/399 |
| 4,255,458 A | * | 3/1981 | Roselius et al. | 426/424 |
| 4,324,840 A | * | 4/1982 | Katz | 426/422 |
| 4,411,923 A | * | 10/1983 | Hubert et al. | 426/271 |
| 4,673,530 A | | 6/1987 | Hara | |
| 4,976,979 A | * | 12/1990 | Klima et al. | 426/427 |
| 5,393,329 A | * | 2/1995 | Inagaki et al. | 96/131 |
| 6,210,679 B1 | * | 4/2001 | Bailey et al. | 424/729 |
| 2003/0083270 A1 | * | 5/2003 | Burdick et al. | 514/27 |
| 2003/0185950 A1 | * | 10/2003 | Niino et al. | 426/435 |

FOREIGN PATENT DOCUMENTS

| CN | 1141727 A | * | 2/1997 |
| CN | 1304919 A | * | 7/2001 |
| CN | 1421426 A | * | 6/2003 |
| DE | 34 14 767 | | 11/1985 |
| DE | 3414767 A | * | 11/1985 |
| EP | 167399 A | * | 1/1986 |
| EP | 0 423 419 A1 | | 4/1991 |
| EP | 1120379 A1 | * | 8/2001 |
| EP | 1 527 693 | | 5/2005 |
| EP | A-1557097 | | 7/2005 |
| JP | 71039058 B | * | 11/1971 |
| JP | 48-4692 | | 1/1973 |
| JP | 59-219384 | | 12/1984 |
| JP | 60-156614 | | 8/1985 |
| JP | 01-289448 | | 11/1989 |
| JP | 02041165 A | * | 2/1990 |
| JP | 3-133928 | | 6/1991 |
| JP | 04182479 A | * | 6/1992 |
| JP | 04-300836 | | 10/1992 |
| JP | 04-352726 | | 12/1992 |
| JP | 06-009607 | | 1/1994 |
| JP | 06-142405 | | 5/1994 |
| JP | 6-142405 | | 5/1994 |
| JP | 07-238078 | | 9/1995 |
| JP | 10004919 A | * | 1/1998 |
| JP | 10-067771 | | 3/1998 |
| JP | 11-140092 | | 5/1999 |
| JP | 2000-166466 | | 6/2000 |
| JP | 2002153211 A | * | 5/2002 |
| JP | 2003-219799 | | 8/2003 |
| JP | 2003-219800 | | 8/2003 |
| JP | 2003-225053 | | 8/2003 |
| JP | 2004-147508 | | 5/2004 |
| JP | 2004-222719 | | 8/2004 |

OTHER PUBLICATIONS

Machine Translation of CN1141727 which was published Feb. 1997.*
Machine Translation of JP2000-166466, which was published Jun. 20, 2000.*
Translation of CN 1421426, which was published Jun. 2003.*
Machine Translation of JP10-004919, which was published Jan. 1998.*
Machine Translation of DE3414767, which was published Nov. 7, 1985.*
"Kuraraycoal" Feb. 3, 2003 http://web.archive.org/web/

(Continued)

*Primary Examiner* — Viren Thakur
(74) *Attorney, Agent, or Firm* — Oblon, Spivak, McClelland, Maier & Neustadt, L.L.P.

(57) ABSTRACT

To provide a packaged high-catechin beverage in which a low-caffeine green tea extract is added. A packaged beverage containing from 0.03 to 1.0 wt % of non-polymer catechins, in which a low-caffeine green tea extract obtained by a method of brining a green tea extract into contact with a 91/9 to 97/3 by weight mixture of an organic solvent and water, activated carbon, and acid clay or activated clay is added.

10 Claims, No Drawings

OTHER PUBLICATIONS

20030203171612/http://www.kuraraychemical.com/Products/Products.htm Feb.*
Chang et al. "Separation of Catechins from Green Tea Using Carbon Dioxide Extraction." Food Chemistry 68, 2000, pp. 109-113.*
JP2000-166466 Translation, Aug. 2010.*
CN1421426 Translation, Jun. 2009.*
Lin et al. "Factors Affecting the Levels of Tea Polyphenols and Caffeine in Tea Leaves", J.Agric. FOod Chem. 2003, 51, 1864-1873.*
Pan et al. "Microwave assisted extraction of tea polyphenols and tea caffeine from green tea leaves".*
CN1141727 Translation Aug. 2010.*
Lin et al. "Determination of Tea Polyphenols and Caffeine in Tea Flowers (*Camellia sinensis*) and Their Hydroxyl Radical Scavenging and Nitric Oxide Suppressing Effects." J.Agric.Food Chem. 2003, 51, 975-980.*
U.S. Appl. No. 12/300,800, filed Nov. 14, 2008, Satake, et al.

* cited by examiner

US 8,088,429 B2

PACKAGE DRINK

FIELD OF THE INVENTION

This invention relates to a packaged beverage in which a low-caffeine green tea extract is added, and also to a process for production of the low-caffeine green tea extract.

BACKGROUND OF THE INVENTION

Catechins are known to have a suppressing effect on increase in cholesterol level and an inhibitory effect on α-amylase activity (Patent Documents 1 to 2). To develop such physiological effects of catechins, it is necessary for an adult to drink 4 to 5 cups of tea per day. Accordingly, there is a desire for technology that permits addition of catechins at a high concentration to beverages to facilitate ingestion of a large amount of catechins. As one of the methods, catechins are added in a dissolved form to a beverage by using a concentrate of green tea extract (Patent Document 3) or the like.

As processes for extracting catechins with a stable taste from green tea or semi-fermented or fermented tea leaves, there are known a two-step extraction process in which extraction is conducted with slightly warm water, and subsequent to heating, extraction is conducted again and an extraction process under strongly acidic conditions (Patent Documents 4-6). However, these extraction processes are limited to the extraction of catechins from tea leaves, and are intended to achieve only stabilization of a taste of a purified product and maintenance of a good taste.

Further, catechins are generally known to be sparingly soluble in organic solvents. It is also known that the extraction of catechins can be promoted in a weakly acidic range. A high proportion of an organic solvent, however, involves such a problem that the efficiency of extraction of catechins is substantially lowered (Patent Document 7).

In tea leaves, however, caffeine component is also contained generally at from 2 to 4 wt % although catechins are contained in an amount as much as about 15 wt %. As caffeine exhibits a central stimulant effect, it is used for the suppression of sleepiness. On the other hand, its excessive ingestion is considered to bring about adverse effects such as nervosity, nausea and hyposomnia. Investigations have, therefore, been made for processes that selectively remove only caffeine from caffeine-containing compositions.

Proposed is, for example, a process in which caffeine is selectively removed by bringing a caffeine-containing, aqueous solution into contact with activated clay or acid clay (Patent Document 8). However, this process is accompanied by such a problem that the color may be deteriorated in some instances, although caffeine can be selectively removed by simply using activated clay or acid clay.

[Patent Document 1] JP-A-60-156614
[Patent Document 2] JP-A-03-133928
[Patent Document 3] JP-A-59-219384
[Patent Document 4] JP-A-2003-219799
[Patent Document 5] JP-A-2003-219800
[Patent Document 6] JP-A-2003-225053
[Patent Document 7] JP-A-2004-147508
[Patent Document 8] JP-A-06-142405

The present invention provides a packaged beverage containing from 0.03 to 1.0 wt % of non-polymer catechins, wherein the packaged beverage contains a low-caffeine green tea extract obtained by a method of bringing a green tea extract into contact with a 91/9 to 97/3 by weight mixture of an organic solvent and water (i.e. a mixture of an organic solvent and water at a weight ratio of 91/9 to 97/3), activated carbon, and acid clay or activated clay.

The present invention also provides a process for producing a low-caffeine green tea extract containing from 25 to 90 wt % of non-polymer catechins based on a dry weight of the extract, which comprises bringing a green tea extract into contact with a 91/9 to 97/3 by weight mixture of an organic solvent and water, activated carbon, and acid clay or activated clay.

The present invention further provides a low-caffeine green tea extract, wherein the low-caffeine green tea extract contains from 40 to 90 wt % of non-polymer catechins based on a solid content of the low-caffeine green tea extract, and a weight ratio of the non-polymer catechins to caffeine is from 25 to 200.

The present invention still further provides a process for selectively removing caffeine from a caffeine-containing catechin composition, which comprises dispersing a green tea extract in a 91/9 to 97/3 by weight mixture of an organic solvent and water and bringing the resulting dispersion into contact with activated carbon and acid clay or activated clay.

EMBODIMENTS OF THE INVENTION

The present invention relates to a method for selectively removing caffeine from a green tea extract without significantly changing the composition of catechins and moreover, without deteriorating the color, and also to a low-caffeine green tea extract produced by the method and a packaged beverage, especially a packaged non-tea beverage in which the low-caffeine green tea extract is added.

The present invention further relates to a process for selectively removing caffeine from a green tea extract without significantly changing the composition of catechins and moreover, without deteriorating the color.

The present inventors have found that a low-caffeine green tea extract can be obtained as a purified green tea extract, in which caffeine has been selectively removed without significantly changing the composition of catechins, and moreover, without deteriorating the color, by bringing a green tea extract into contact with a 91/9 to 97/3 by weight mixture of ethanol and water, activated carbon, and acid clay or activated clay, and also that the low-caffeine green tea extract provides high-catechin beverages, especially packaged high-catechin non-tea beverages with a good taste.

According to the present invention, it is possible to selectively remove caffeine from a green tea extract without significantly changing the compositions of catechins, and moreover, without changing the color, and to efficiently extract non-polymer catechins. In addition, the addition of the resulting low-caffeine green tea extract enables obtention of a packaged beverage which is low in caffeine content, contains catechins at a high concentration, and is good in color and taste.

The green tea extract for use in the present invention contains one or more non-polymer catechins. The term "non-polymer catechins" as used herein is a generic term which collectively encompasses non-epicatechins such as catechin, gallocatechin, catechin gallate and gallocatechin gallate, and epicatechins such as epicatechin, epigallocatechin, epicatechin gallate and epigallocatechin gallate. On the other hand, the term "gallates" is a generic term which collectively embraces catechin gallate, gallocatechin gallate, epicatechin gallate and epigallocatechin gallate among the above-described non-polymer catechins. Further, the term "gallocatechins" is a generic term which collectively encompasses gallocatechin, gallocatechin gallate, epigallocatechin and epigallocatechin gallate among the above-described non-polymer catechins. The term "gallocatechins percentage" means the weight percentage of the gallocatechins in these non-polymer catechins.

As green tea extracts usable in the present invention, extracts obtained from tea leaves such as green tea, black tea and oolong tea can be mentioned. In addition, mixtures of caffeine derived from other caffeine-containing plants such as coffee with tea extracts are also usable. Among such green tea extracts containing non-polymer catechins, preferred are those obtained by drying or concentrating extracts from green tea leaves.

Tea leaves for use in the present invention include, more specifically tea leaves manufactured from tea leaves of the Genus *Camellia*, for example, *C. sinensis* and *C. assamica*, and the Yabukita variety or their hybrids. Such manufactured tea leaves include green teas such as sencha (middle-grade green tea), bancha (coarse green tea), gyokuro (shaded green tea), tencha (powdered tea) and kamairicha (roasted tea).

A tea leaf extract can be obtained by a method such as stirring extraction. An organic acid or organic acid salt such as sodium ascorbate can be added beforehand to water upon extraction. It is also possible to make combined use of boiling deaeration or an extraction method which is conducted while flowing an inert gas such as nitrogen gas to eliminate dissolved oxygen, that is, under a so-called non-oxidizing atmosphere. The extract obtained as described above is dried to provide the green tea extract for use in the present invention. Forms of the green tea extract include liquid, slurry, semi-solid and solid forms. From the viewpoint of dispersibility in ethanol, a slurry, semi-solid or solid form is preferred.

Instead of employing, as a green tea extract for use in the present invention, a dried tea leaf extract, it is also possible to employ a concentrate of a tea extract in a form dissolved in or diluted with water or to employ an extract from tea leaves and a concentrate of a tea extract in combination.

The term "the concentrate of a tea extract" as used herein means a concentrate of an extract obtained from tea leaves with hot water or a water-soluble organic solvent, and includes, for example, those prepared by the processes disclosed in JP-A-59-219384, JP-A-04-20589, JP-A-05-260907, JP-A-05-306279 and the like.

As the green tea extract, it is possible to use specifically a commercially-available crude solid catechin preparation such as "Polyphenon" (product of Tokyo Food Techno Co., Ltd.), "TEAFURAN" (product of ITO EN, LTD.) or "SUNPHENON" (product of Taiyo Kagaku Co., Ltd.).

As the green tea extract, it is also possible to use an extract obtained from tea leaves belonging to the Genus *Camellia* and subjected beforehand to a treatment of contacting with carbon dioxide in a supercritical state. The tea leaves for use in supercritical extraction can be either raw tea leaves or manufactured tea leaves insofar as they belong to the Genus *Camellia*. As the manufactured tea leaves, non-fermented tea is more preferred. Preferred examples of steamed tea leaves include sencha (middle-grade green tea), fukamushicha (deep-steamed green tea), gyokuro (shaded green tea), kabusecha (partially shaded green tea), mushi-tamaryokucha (steamed, rounded, beads-shaped green tea), and bancha (coarse green tea). Preferred examples of roasted tea leaves, on the other hand, include kamairi-tamaryokucha (roasted, rounded, beads-shaped green tea) and Chinese green tea. As manufactured tea leaves, steamed tea leaves or dipped tea leaves are preferred from the standpoint of avoiding generation of an additional flavor and taste derived from tea leaves during roasting.

In this method, an extract containing non-polymer catechins is obtained from tea leaves available as a residue in the supercritical extraction. There have conventionally been several techniques for obtaining flavor components from tea leaves by supercritical extraction (JP-A-2001-293076, JP-A-10-77496, JP-A-06-133726, and JP-A-06-184591). Any of these techniques uses a supercritical extract of tea leaves, however, and there is no description as to a technique that makes use of residual tea leaves after supercritical extraction or as to the components that remain in the residual tea leaves.

A process for production of a tea extract from tea leaves, which belong to the Genus *Camellia* and have been subjected to a treatment to contact with carbon dioxide in its supercritical state, includes specifically (A) a step of moistening green tea leaves, (B) a step of treating the green tea leaves with carbon dioxide in its supercritical state, and (C) a step of extracting a green tea extract from the tea leaves. Each of these steps will hereinafter be described.

In the step (A), from 0.2 to 0.4 weight part of a 75:25 to 99.5:0.5 mixture of ethanol and water is at first added to 1 weight part of the green tea leaves to moisten the green tea leaves. Without this moistening step of the green tea leaves with the 75:25 to 99.5:0.5 mixture of ethanol and water, elimination of a green tea flavor in the step (B) cannot be achieved sufficiently. In view of the effect of elimination of the green tea flavor and the efficiency of extraction, it is preferred to add from 0.2 to 0.4 weight part of the 75:25 to 99.5:0.5 mixture of ethanol and water to 1 weight part of the green tea leaves.

The ratio of ethanol to water in the mixture is preferably from 75:25 to 99.5:0.5, more preferably from 80:20 to 99.5:0.5, still more preferably from 80:20 to 90:10. The mixture of ethanol and water is added in an amount of from 0.2 to 0.4 weight part, preferably from 0.3 to 0.4 weight part.

The green tea leaves to which the above-described predetermined amount of the mixture of ethanol and water has been added is preferably left to stand at from 0 to 100° C. for 0.5 hour or longer to have the green tea leaves moistened sufficiently.

In the step (B), carbon dioxide in a supercritical state in which a 75:25 to 99.5:0.5 mixture of ethanol and water has been added is preferably brought into contact with the moistened green tea leaves. According to the step (B), the water content of the green tea leaves can be retained constant so that the green tea flavor in the green tea leaves can be efficiently eliminated. On the other hand, the catechins in the green tea remain substantially completely in the green tea leaves, and are not impaired by the above operation.

The ratio of ethanol to water in the mixture to be used is preferably from 75:25 to 99.5:0.5, more preferably from 75:25 to 95:5, still more preferably from 80:20 to 90:10. The mixture of ethanol and water is added in an amount of from 0.02 to 0.04 weight part, preferably from 0.03 to 0.04 weight part per weight parts of carbon dioxide.

As to the carbon dioxide to be used, elimination of green tea flavor components can be efficiently achieved insofar as carbon dioxide is in a supercritical state (pressure: 7 MPa or higher, temperature: 31° C. or higher). From the standpoints of the efficiency of elimination of bitter components and green tea flavor, however, carbon dioxide at from 20 to 50 MPa and at 35 to 100° C., particularly at from 30 to 40 MPa and at 60 to 80° C. is preferred. Carbon dioxide can be used in a proportion of preferably 20 weight parts or more, more preferably from 20 to 250 weight parts, still more preferably from 50 to 150 weight parts per weight part of the green tea leaves.

Ethanol and/or water and supercritical carbon dioxide is brought into contact with the green tea leaves preferably at the same time. For example, an aqueous ethanol solution and supercritical carbon dioxide may be brought into contact with the tea leaves at the same time, or an aqueous ethanol solution and supercritical carbon dioxide may be mixed together in advance, and may then be brought into contact with the green tea leaves. To bring ethanol and/or water and supercritical carbon dioxide into contact with the green tea leaves, use of an ordinary supercritical extraction apparatus is preferred. In general, the above-described contact may be effected preferably at a feed rate of from 10 to 25 weight parts/hour of supercritical carbon dioxide per weight part of green tea leaves to retain the water content of the green tea leaves although the feed rate may vary depending on the capacity of the apparatus.

In the step (C), it is preferred to conduct the extraction from the green tea leaves which have been brought into contact with the supercritical carbon dioxide by using from 10 to 150 weight parts of water per weight part of the green tea leaves. To maximize the efficiency of extraction of water-soluble components such as catechins, water may be used preferably in an amount of from 20 to 100 weight parts, more preferably in an amount of from 20 to 50 weight parts.

The extraction in the step (C) can be conducted under usual extraction conditions. Upon conducting the extraction from the green tea leaves, the temperature can be changed as needed depending on the kind of the tea leaves. The temperature is preferably, for example, from 60 to 90° C. in the case of sencha (middle-grade green tea) or gyokurocha (shaded green tea), or from 50 to 60° C. in the case of gyokuro (shaded green tea) or kabusecha (partially shaded green tea). In the case of bancha (coarse tea), on the other hand, a temperature in a range of from 90° C. to boiling water can be used. The time of extraction from the green tea leaves is preferably from 1 to 60 minutes, more preferably from 1 to 40 minutes, still more preferably from 1 to 30 minutes. In the case of a process for production of an extract from middle-grade sencha leaves, for example, an extract can be obtained by adding the tea leaves into ion-exchanged water heated at 65° C., stirring them for 2 minutes or so, leaving them to stand for 2 minutes or so, filtering out the green tea leaves, and then filtering out fragmented tea leaves with a flannel filter cloth.

As the green tea extract for use in the present invention, a green tea extract containing preferably from 25 to 90 wt %, more preferably from 25 to 70 wt %, still more preferably from 40 to 70 wt % of non-polymer catechins on a dry weight basis can be used preferably, because taste components other than the non-polymer catechins still remain in the green tea extract.

By the method of bringing the resulting green tea extract into contact with the 91/7 to 97/3 by weight mixture of the organic solvent and water, activated carbon, and acid clay or activated clay, the green tea extract is purified to give a low-caffeine green tea extract.

As the organic solvent for use in the production of the low-caffeine green tea extract in the present invention, ethanol, methanol, acetone, ethyl acetate or the like can be mentioned. Among these, a hydrophilic organic solvent such as methanol, ethanol or acetone is preferred, with ethanol being more preferred in view of the use of the low-caffeine green tea extract in foods.

Concerning the organic solvent and water to be used in the production of the low-caffeine green tea extract in the present invention, it is preferred to adjust their weight ratio to a range of preferably from 91/9 to 97/3, more preferably to from 92/8 to 96/4, still more preferably from 92/8 to 95/5. The above-mentioned range is preferred from the standpoints of the extraction efficiency of catechins, the purification and long-term drinkability of the green tea extract, fractionation conditions for the recovered organic solvent and the like.

In the present invention, it is preferred to conduct the processing by adding from 10 to 40 weight parts, more preferably from 10 to 30 weight parts, particularly preferably from 15 to 30 weight parts of the green tea extract (on a dry weight basis) to 100 weight parts of the mixture of the organic solvent and water because the green tea extract can be processed efficiently.

No particular limitation is imposed on the activated carbon to be used in the present invention insofar as it is generally used on an industrial level. Usable examples include commercially-available products such as "ZN-50" (product of Hokuetsu Carbon Industry Co., Ltd.), "KURARAY COAL GLC", "KURARAY COAL PK-D" and "KURARAY COAL PW-D" (products of Kuraray Chemical K.K.), and "SHIROWASHI AW50", "SHIROWASHI A", "SHIROWASHI M" and "SHIROWASHI C" (products of Takeda Pharmaceutical Company Limited).

The pore volume of the activated carbon is preferably from 0.01 to 0.8 mL/g, more preferably from 0.1 to 0.7 mL/gm. The activated carbon having a specific surface area in a range of from 800 to 1,300 $m^2/g$, particularly from 900 to 1,200 $m^2/g$ is preferred. It is to be noted that these physical values are those determined by the nitrogen adsorption method.

The activated carbon can be added preferably in a proportion of from 0.5 to 5 weight parts, particularly in a proportion of from 0.5 to 3 weight parts to 100 weight parts of the mixture of the organic solvent and water, because such a proportion results in high decaffeination efficiency and low cake resistance in the filtration step.

Acid clay and activated clay for use in the present invention both contain, as general chemical components, $SiO_2$, $Al_2O_3$, $Fe_2O_3$, CaO, MgO, etc., and those having a $SiO_2/Al_2O_3$ ratio of from 3 to 12, particularly from 4 to 9 are preferred. Also preferred are those which contain from 2 to 5 wt % of $Fe_2O_3$, from 0 to 1.5 wt % of CaO and from 1 to 7 wt % of MgO.

Activated clay is obtained by treating a naturally-occurring acid clay (montmorillonite clay) with a mineral acid such as sulfuric acid, and is a compound having a porous structure of large specific surface area and adsorbability. Further treatment of acid clay with an acid is known to change its specific surface area so that its decoloring ability is improved and its physical properties are modified.

The specific surface area of acid clay or activated clay is preferably from 50 to 350 $m^2/g$ although it varies depending on the degree of the acid treatment or the like, and its pH (5 wt % suspension) is preferably from 2.5 to 8, particularly from 3.6 to 7. Usable examples of acid clay include commercially-available products such as "MIZUKA ACE #600" (product of Mizusawa Chemical Industries, Ltd.).

The weight ratio of activated carbon to acid clay or activated clay is appropriately from 1 to 10 of acid clay or activated clay to 1 activated carbon, with the weight ratio of activated carbon:acid clay or activated clay=1:1 to 1:6 being preferred.

The process of the present invention for the production of the low-caffeine green tea extract is preferably (a) a process in which the green tea extract is dissolved in the mixture of the organic solvent and water and is then brought into contact with activated carbon and acid clay or activated clay, or (b) a process in which a dispersion of activated carbon and acid clay or activated clay in a mixture of the organic solvent and water, as well as the green tea extract are subjected to a treatment for contacting them with each other. It is to be noted that as the feed green tea extract, one obtained by the above-described supercritical extraction may also be used.

No particular limitation is imposed on the order of contact among the green tea extract, activated carbon, and acid clay or activated clay. Activated clay and acid clay or activated clay may be brought into contact with each other at the same time, or the green tea extract and acid clay or activated clay may first be brought into contact with each other, followed by contact with activated carbon.

For obtaining a purified green tea extract with non-polymer catechins efficiently extracted therein, it is preferred to effect the contact between the green tea extract and acid clay or activated clay by adjusting the pH to a range of from 4 to 6. Upon effecting the contact, an organic acid such as citric acid, lactic acid, tartaric acid, succinic acid or malic acid is preferably added at a weight ratio of the organic acid to the non-polymer catechins (organic acid/non/polymer catechins) in a range of from 0.02 to 0.20.

When producing the low-caffeine green tea extract by dispersing the green tea extract in the mixture of the organic acid and water and then subjecting the resulting dispersion to a treatment to contact it with activated carbon and acid clay or activated clay, no particular limitation is imposed on the manner of dissolution of the green tea extract in the mixture of the organic solvent and water insofar as the weight ratio of the organic solvent to water upon final treatment of the caffeine-containing catechin composition is in the range of from 91/9 to 97/3. For example, the weight ratio of the organic solvent to water may be brought into the range of from 91/9 to 97/3 by gradually adding the organic solvent after dissolving the green tea extract in water, or water may be gradually added to give a similar ratio after suspending the green tea extract in the organic solvent. From the standpoint of extraction efficiency, however, it is preferred to gradually add the organic solvent subsequent to the dissolution in water.

As to the time over which a required amount of water or the organic solvent is added, it is preferred to slowly add dropwise water or the organic solvent over a time of from approximately 10 to 30 minutes. To improve the efficiency of extraction of catechins, it is also preferred to effect the dropwise addition under stirring. It is more preferred to include an aging time of from 10 to 120 minutes or so after the completion of the dropwise addition of water.

These processing can be conducted at from 10 to 60° C., preferably from 10 to 50° C., more preferably from 10 to 40° C.

Acid clay or activated clay can be added preferably in a proportion of from 2.5 to 25 weight parts, particularly in a proportion of from 2.5 to 15 weight parts to 100 weight parts of the mixture of the organic solvent and water. The addition of acid clay or activated clay in an unduly small proportion leads to deterioration in decaffeination efficiency, while the addition of acid clay or activated clay in an excessively large proportion leads to increase in the cake resistance in the filtration step. It is, therefore, not preferred to add acid clay or activated clay in a proportion outside the above-described range.

When mixing the green tea extract in contact with the dispersion of acid clay or activated clay in the mixture of the organic solvent and water in the present invention, the mixing weight ratio of the acid clay or activated clay to the green tea extract is preferably from 0.9 to 5.0, more preferably from 1.5 to 3.0 in terms of the acid clay or activated clay/non-polymer catechins value. The addition of acid clay or activated clay in an unduly small proportion leads to deterioration in decaffeination efficiency, while the addition of acid clay or activated clay in an excessively large proportion leads to increase in the cake resistance in the filtration step. It is, therefore, not preferred to add acid clay or activated clay at a ratio outside the above-described range.

As to the temperature at which the dispersion is brought into contact with the green tea extract, it is preferred at first to set the temperature at from 10 to 30° C. and then to raise the temperature to from 40 to 60° C. because dissolution of the green tea extract can be promoted and the efficiency of extraction of catechins into the dispersion can be also promoted.

After the contact of the green tea extract with the dispersion, the resulting mixture is further brought into contact with activated carbon. Preferably, the green tea extract and the dispersion is first mixed together to bring them into contact with each other, and subsequent to filtration, the filtrate is then subjected to a treatment to contact it with activated carbon.

The treatment of the green tea extract to contact it with activated carbon and acid clay or activated clay can be conducted by any method such as a batchwise treatment method or a continuous treatment method making use of a column. As to a method for bringing the green tea extract into contact with activated carbon, the contact may be effected preferably by a continuous treatment through a column packed with activated carbon. Adopted in general is a method in which powdery activated carbon or the like is added, the resulting mixture is stirred to selectively adsorb caffeine, and subsequent to selective adsorption of caffeine by a filtering operation, filtration is conducted to obtain a decaffeinated filtrate, or a method in which caffeine is selectively adsorbed by a continuous treatment using a column packed with granular activated carbon or the like.

After the contact of the green tea extract with activated carbon and acid clay or activated clay, distillation such as reduced-pressure distillation is conducted to remove the organic solvent such as ethanol from the mixture of the organic solvent and water. The treated green tea extract can be either in a liquid form or in a solid form. To prepare it into a solid form, it may be formed into powder by a method such as freeze drying or spray drying.

The purified green tea extract (low-caffeine green tea extract), which has been subjected to the decaffeination treatment according to the present invention, may preferably remain substantially unchanged in the composition of the non-polymer catechins containing therein compared with the composition before the treatment. The yield of the non-polymer catechins in the mixture of the organic solvent and water before and after the treatment is preferably 60 wt % or more, more preferably 65 wt % or more, still more preferably 70 wt % or more, particularly preferably 80 wt % or more.

Further, the content of the gallates consisting of catechin gallate, epicatechin gallate, gallocatechin gallate and epigallocatechin gallate in the low-caffeine green tea extract is preferably from 45 to 100 wt %, more preferably from 50 to 98 wt % of the whole non-polymer catechins from the standpoint of the effectiveness of physiological effects of the non-polymer catechins.

The concentration of caffeine in the low-caffeine green tea extract is preferably from 25 to 200, more preferably from 30 to 150, still more preferably from 30 to 100, particularly preferably from 30 to 60 relative to the non-polymer catechins, that is, in terms of the non-polymer catechins/caffeine.

In the solid content of the low-caffeine green tea extract, the non-polymer catechins amount to preferably from 25 to 90 wt %, more preferably from 30 to 90 wt %, still more preferably from 35 to 90 wt %.

In the solid content of the low-caffeine green tea extract, free amino acids and proteins may also amount preferably to from 0 to 5.0 wt % in total. The weight ratio of the non-polymer catechins to the total amount of the free acids and proteins (the non-polymer catechins/(the free amino acids+proteins) is preferably from 15 to 25.

The resulting low-caffeine green tea extract, despite its low caffeine concentration, still contains non-polymer catechins at a high concentration, has a good color, and further, is substantially free of the flavor of green tea. Therefore, packaged beverages in which the low-caffeine green tea extract is incorporated are useful particularly as non-tea beverages such as sports drinks and isotonic drinks.

The packaged beverage according to the present invention contains non-polymer catechins (A) dissolved in water in an amount of from 0.03 to 1.0 wt %, preferably from 0.04 to 0.5 wt %, more preferably from 0.06 to 0.4 wt %, still more preferably from 0.07 to 0.4 wt %, particularly preferably from 0.08 to 0.3 wt %, even more preferably from 0.09 to 0.3 wt %, still even more preferably from 0.1 to 0.3 wt %. Insofar as the content of non-polymer catechins falls within the above-described range, a great deal of non-polymer catechins can be taken with ease, and from the standpoint of the color tone of the beverage shortly after its preparation, this content range is also preferred. The concentration of the non-polymer catechins can be adjusted by the amount of the green tea extract to be incorporated.

Further, the daily intake of green tea required for an adult to exhibit the effects of the promotion of accumulated fat burning, the promotion of dietary fat burning and the promotion of β-oxidation gene expression in the liver is preferably 300 mg or more, more preferably 450 mg or more, still more preferably 500 mg or more in terms of non-polymer catechins. Specifically, it has been confirmed that an anti-puffiness effect and/or visceral fat reducing effect can be brought about by ingesting a beverage which contains 483 mg, 555 mg or 900 mg of non-polymer catechins per package (JP-A-2002-326932).

Therefore, the daily intake of the packaged beverage according to the present invention for an adult can also be preferably 300 mg or more, more preferably 450 mg or more, still more preferably 500 mg or more in terms of non-polymer catechins. From the standpoint of assuring the required daily intake amount, the non-polymer catechins is contained in an amount of preferably 300 mg or more, more preferably 450 mg or more, still more preferably 500 mg or more in the packaged beverage according to the present invention.

The weight ratio of the non-polymer catechins to caffeine contained in the packaged beverage according to the present invention is preferably from 25 to 200, more preferably from 30 to 200, still more preferably from 30 to 150, particularly preferably from 30 to 100.

The packaged beverage according to the present invention may also contain sodium ions and/or potassium ions. Beverages of the present invention containing such ions are useful in the form of drinks such as sports drinks and isotonic drinks. The term "sports drink" is generally defined to mean a drink that can promptly replenish water and minerals lost in the form of sweat during physical exercise.

Sodium and potassium can be mentioned as primary physiological electrolytes. These ion ingredients can be incorporated in their corresponding water-soluble ingredients or inorganic salts. They are also found in fruit juices and tea extracts. The amount of an electrolyte or ion ingredient in the packaged beverage according to the present invention is its content in the final packaged beverage ready for drinking. The concentration of an electrolyte is expressed in terms of "ion concentration". In the beverage according to the present invention, a potassium ion ingredient can be added in the form of a salt such as potassium chloride, potassium carbonate, potassium sulfate, potassium acetate, potassium hydrogencarbonate, potassium citrate, potassium phosphate, potassium hydrogen phosphate, potassium tartrate, potassium sorbate or a mixture thereof or as a component of an added fruit juice or tea. In the packaged beverage according to the present invention, potassium ions can be contained in an amount of preferably from 0.001 to 0.2 wt %, more preferably from 0.002 to 0.15 wt %, even more preferably from 0.003 to 0.12 wt %. Similarly, a sodium ion ingredient can also be added as a readily-available sodium salt such as sodium chloride, sodium carbonate, sodium hydrogencarbonate, sodium citrate, sodium phosphate, sodium hydrogenphosphate, sodium tartrate, sodium benzoate or a mixture thereof or as a component of an added fruit juice or tea. A lower sodium ion concentration is desired from the standpoint of facilitating the absorption of water owing to osmotic pressure. Preferably, however, the sodium ion concentration should be such a level as to avoid suction of water into the intestine from the body by osmotic pressure. The sodium ion concentration required to achieve such level can preferably be lower than the sodium ion concentration in the plasma. In the packaged beverage according to the present invention, sodium ions can be contained at a concentration of preferably from 0.001 to 0.5 wt %, more preferably from 0.002 to 0.4 wt %, most preferably from 0.003 to 0.2 wt %. In addition to potassium ions and sodium ions, from 0.001 to 0.5 wt %, preferably from 0.002 to 0.4 wt %, still more preferably from 0.003 to 0.3 wt % of chloride ions can also be incorporated in the packaged beverage according to the present invention. A chloride ion ingredient can be added in the form of a salt such as sodium chloride or potassium chloride. Further, trace ions such as calcium, magnesium, zinc and/or iron ions can also be added. These ions can also be added in the form of salt or salts. The total amount of ions existing in the beverage includes not only an amount of ions added but also an amount of ions naturally existing in the beverage. When sodium chloride is added, for example, the amounts of sodium ions and chloride ions in the added sodium chloride are included in the total amount of ions in the beverage.

Depending upon the situation of drinking, an excessively low concentration of sodium ions and potassium ions may fail to provide a fulfilled feeling in taste and to achieve an effective replenishment of minerals, and therefore, may not be preferred. An unduly high concentration of sodium ions and potassium ions, on the other hand, leads to strong tastes of the salts themselves and is not preferred for long-term drinking.

In the packaged beverage according to the present invention, a sweetener may also be used to improve the taste. As the sweetener, an artificial sweetener, carbohydrate or glycerol (for example, glycerin) can be used. The content of such a sweetener in the packaged beverage according to the present invention is preferably from 0.0001 to 20 wt %, more preferably from 0.001 to 15 wt %, even more preferably from 0.001 to 10 wt % from the standpoints of the balance among sweetness, sourness and saltiness, avoidance of excessive sweetness and a reduction in the feeling of being caught in the throat and an improvement in the feeling as the beverage passes down the throat.

As the sweeteners usable in the packaged beverage according to the present invention, use of an artificial sweetener is preferred. Example of the artificial sweeteners usable in the present invention include high-sweetness sweeteners such as saccharin, saccharin sodium, aspartame, acesulfame-K, sucralose and neotame; and sugar alcohols such as sorbitol, erythritol and xylitol. As commercial products, "SLIM-UP SUGAR" composed of aspartame, "LAKANTO-S" containing erythritol, and "PALSWEET" composed of erythritol and aspartame can be used.

When the aimed packaged beverage is intended to replenish energy, it is preferred to use a carbohydrate sweetener.

As the carbohydrate sweeteners usable in the present invention, soluble carbohydrates can be employed. A soluble carbohydrate serves not only as a sweetener but also as an energy source. Upon choosing a carbohydrate for use in the beverage according to the present invention, it is preferred to take a sufficient gastric excretion rate and intestinal absorption rate into consideration.

The carbohydrate can be a mixture of glucose and fructose, or a carbohydrate hydrolyzable into glucose and fructose or capable of forming glucose and fructose in the digestive tract. The term "carbohydrate" as used herein includes monosaccharides, disaccharides, oligosaccharides, conjugated polysaccharides, and mixtures thereof.

Monosaccharides usable in the present invention include tetroses, pentoses, hexoses and ketohexoses. Examples of the hexoses are aldohexoses such as glucose known as grape sugar. The content of glucose in the packaged beverage can be preferably from 0.0001 to 20 wt %, more preferably from 0.001 to 15 wt %, still more preferably from 0.001 to 10 wt %. Fructose known as fruit sugar is a ketohexose. The content of fructose in the packaged beverage according to the present invention can be preferably from 0.0001 to 20 wt %, more preferably from 0.001 to 15 wt %, particularly preferably from 0.001 to 10 wt %.

Preferred in the beverage according to the present invention is a single artificial sweetener system or a combination of an artificial sweetener and a glucose compound or a combination of an artificial sweetener and a fructose compound.

As a carbohydrate sweetener for use in the present invention, a soluble carbohydrate can be employed. As an oligosaccharide, a carbohydrate which produces these two kinds of monosaccharides in vivo (specifically, sucrose, maltodextrin, corn syrup, and fructose-rich corn syrup) can be mentioned. It is a disaccharide that is an important type of the saccharide. An illustrative disaccharide is sucrose known as cane sugar or beet sugar. The content of sucrose in the packaged beverage according to the present invention can be preferably from 0.001 to 20 wt %, more preferably from 0.001 to 15 wt %, particularly preferably from 0.001 to 10 wt %.

The pH of the packaged beverage according to the present invention can be preferably from 2 to 6, more preferably from 2 to 5, still more preferably from 3 to 4.5 from the standpoint of the stability of catechins. An excessively low pH provides the beverage with a stronger sour taste and pungent smell. An unduly high pH, on the other hand, fails to achieve a harmony in flavor and leads to reduction in taste. Such an excessively low pH or unduly high pH is, therefore, not preferred.

Addition of a bitterness suppressor to the packaged beverage according to the present invention facilitates its drinking, and therefore, is preferred. Although no particular limitation is imposed on the bitterness suppressor to be used, a cyclodextrin is preferred. As the cyclodextrin, an α-, β- or γ-cyclodextrin or a branched α-, β- or γ-cyclodextrin can be used. In the beverage, a cyclodextrin may be contained preferably in an amount of from 0.005 to 0.5 wt %, more preferably from 0.01 to 0.3 wt %. To the packaged beverage according to the present invention, it is possible to add, either singly or in combination, additives such as antioxidants, flavorings, various esters, organic acids, organic acid salts, inorganic acids, inorganic acid salts, inorganic salts, dyes, emulsifiers, preservatives, seasoning agents, sweeteners, sour seasonings, gums, emulsifiers, oils, vitamins, amino acids, fruit extracts, vegetable extracts, flower honey extracts, pH regulators and quality stabilizers.

To the beverage according to the present invention, one or more of flavorings and fruit juices may preferably be added to improve the taste. In general, the juice of a fruit is called "fruit juice" and a flavoring is called "flavor". Natural or synthetic flavorings and fruit juices can be used in the present invention. They can be selected from fruit juices, fruit flavors, plant flavors, and mixtures thereof. For example, a combination of a fruit juice with a tea flavor, preferably a green tea or black tea flavor provides attractive taste. Preferred fruit juices include apple, pear, lemon, lime, mandarin, grapefruit, cranberry, orange, strawberry, grape, kiwi, pineapple, passion fruit, mango, guava, raspberry and cherry juices. More preferred are citrus juices (preferably, grapefruit, orange, lemon, lime and mandarin juices), mango juice, passion fruit juice, guava juice, and mixtures thereof. Preferred natural flavors include jasmine, chamomile, rose, peppermint, *Crataegus cuneata*, chrysanthemum, water caltrop, sugarcane, bracket fungus of the genus *Fomes* (*Fomes japonicus*), bamboo shoot, and the like. Such a juice can be contained preferably in an amount of from 0.001 to 20 wt %, more preferably from 0.002 to 10 wt % in the beverage according to the present invention. Fruit flavors, plant flavors, tea flavors and mixtures thereof can also be used as fruit juices. Particularly preferred flavorings are citrus flavors including orange flavor, lemon flavor, lime flavor and grapefruit flavor. In addition to such citrus flavors, various other fruit flavors such as apple flavor, grape flavor, raspberry flavor, cranberry flavor, cherry flavor and pineapple flavor are also usable. These flavorings can be derived from natural sources such as fruit juices and balms, or can be synthesized. The term "flavoring" as used herein can also include blends of various flavors, for example, a blend of lemon and lime flavors and blends of citrus flavors and selected spices. Such a flavoring can be added preferably in an amount of from 0.0001 to 5 wt %, more preferably from 0.001 to 3 wt % to the beverage according to the present invention.

The beverage according to the present invention may also contain a sour seasoning as needed. As the sour seasoning, edible acids such as malic acid, citric acid, tartaric acid, and fumaric acid can be mentioned. A sour seasoning may be used to adjust the pH of the beverage according to the present invention. The pH of the beverage according to the present invention is preferably from 2 to 7. As a pH adjuster, an organic or inorganic edible acid can be used. The acid can be used either in a non-dissociated form or in the form of its salt, for example, potassium hydrogenphosphate, sodium hydrogenphosphate, potassium dihydrogenphosphate, or sodium dihydrogenphosphate. Preferred acids can be edible organic acids including citric acid, malic acid, fumaric acid, adipic acid, phosphoric acid, gluconic acid, tartaric acid, ascorbic acid, acetic acid, phosphoric acid, and mixtures thereof. Most preferred acids are citric acid and malic acid. A sour seasoning is useful also as an antioxidant which stabilizes the ingredients in the beverage. Examples of commonly employed antioxidants include ascorbic acid, EDTA (ethylenediaminetetraacetic acid) and salts thereof, and plant extracts.

In the beverage according to the present invention, one or more vitamins can be incorporated further. Preferably, vitamin A, vitamin C, and vitamin E can be added. Other vitamins such as vitamin D and vitamin B may also be added. Minerals can also be used in the beverage according to the present invention. Preferred minerals include calcium, chromium, copper, fluorine, iodine, iron, magnesium, manganese, phosphorus, selenium, silicon, molybdenum, and zinc. Particularly preferred minerals are magnesium, phosphorus, and iron.

As in general beverages, a package used for the packaged beverage according to the present invention can be provided in a conventional form such as a molded package made essentially of polyethylene terephthalate (a so-called PET bottle), a metal can, a paper container combined with metal foils or plastic films, a bottle or the like. The term "packaged beverage" as used herein means a beverage that can be taken without dilution.

The packaged beverage according to the present invention can be produced, for example, by filling the beverage in a package such as a metal can and, when heat sterilization is feasible, conducting heat sterilization under sterilization conditions as prescribed in the Food Sanitation Act. For packages which cannot be subjected to retort sterilization such as PET bottles or paper packages, adopted is a process in which the beverage is sterilized beforehand at a high temperature for a short time under similar sterilization conditions as those described above, for example, by a plate-type heat exchanger or the like, is cooled to a predetermined temperature, and is then filled in a package. Under aseptic conditions, additional ingredients may be added to and filled in a beverage-filled package. It is also possible to conduct such an operation that subsequent to heat sterilization under acidic conditions, the pH of the beverage is brought back to neutral under aseptic conditions or that subsequent to heat sterilization under neutral conditions, the pH of the beverage is brought back to acidic under aseptic conditions.

EXAMPLES

Measurement of Catechins

A high-performance liquid chromatograph (model: "SCL-10Avp") manufactured by Shimadzu Corporation was fitted with a liquid chromatograph column packed with octadecyl-introduced silica gel, "L-Column, TM ODS" (4.6 mm in diameter×250 mm; product of Chemicals Evaluation and Research Institute, Japan). A non-polymer catechin composition was diluted with distilled water, filtered through a filter (0.8 μm), and then subjected to chromatography at a column temperature of 35° C. by the gradient elution method making use of a solution A and a solution B. The solution A, mobile phase, was a solution containing 0.1 mol/L of acetic acid in distilled water, while the solution B was a solution containing 0.1 mol/L of acetic acid in acetonitrile. The measurement was conducted under the conditions of 20 μL sample injection volume and 280 nm UV detector wavelength.

Measurement of Caffeine (Analyzer)

A HPLC system (manufactured by Hitachi, Ltd.) was used.
Plotter: "D-2500", Detector: "L-4200", Pump: "L-7100",
Autosampler: "L-7200", Column: "INTERSIL ODS-2" (2.1 mm in inner diameter×250 mm in length).

(Analytical Conditions)

Sample injection volume: 10 μL

Flow rate: 1.0 mL/min

Detection wavelength of UV spectrophotometer: 280 nm

Eluent A: A 0.1 mol/L solution of acetic acid in water

Eluent B: A 0.1 mol/L solution of acetic acid in acetaonitrile

| Concentration gradient conditions (vol. %) | | |
|---|---|---|
| Time (min) | Eluent A | Eluent B |
| 0 | 97 | 3 |
| 5 | 97 | 3 |
| 37 | 80 | 20 |
| 43 | 80 | 20 |
| 43.5 | 0 | 100 |
| 48.5 | 0 | 100 |
| 49 | 97 | 3 |
| 62 | 97 | 3 |

(Retention Time of Caffeine)

Caffeine: 27.2 min

From each area % determined here, the corresponding wt % was determined based on the standard substance.

Assessment of Color (Analyzer)

"UV MINI1240" (manufactured by Shimadzu Corporation) analyzer was used.

An absorbance value at 450 nm was measured by a spectrophotometer. In the measurement, each purified green tea extract was diluted with ion-exchanged water such that the concentration of catechins was lowered to 100 mg %. Using the sample, the absorbance was measured, and was employed as an index of color.

Visual Assessment of Stability

Each purified green tea extract was diluted with ion-exchanged water such that the concentration of catechins was lowered to 100 mg %. An assessment sample filled in a 50-mL vial was observed for the state of its contents on an illuminator, and the state of the contents was visually ranked.

Measurement of Proteins and Free Amino Acids

Calculation formula for (the amount of proteins and free amino acids):

(Total nitrogen in purified green tea extract−caffeine-form nitrogen)×conversion index Quantitation Method for Total Nitrogen Determined by a nitrogen quantitation conversion method (modified macro-Kjeldahl method) developed following the analytical methods for nutritional components in the Nutrition Labeling Standards (the methods listed in Column 3 of Table 1 attached to the Nutrition Labeling Standards) (Notification No. 146 of the Ministry of Health and Welfare, May 1996).

Caffeine-Form Nitrogen

Determined by converting each caffeine amount, which has been obtained by the above-described measurement of the caffeine amount, into the molecular weight of nitrogen (Mw=54) in the molecular weight of caffeine (Mw=194).

Conversion Index

A conversion index (6.25) is used following the analytical methods for nutritional components in the Nutrition Labeling Standards (the methods listed in Column 3 of Table 1 attached to the Nutrition Labeling Standards) (Notification No. 146 of the Ministry of Health and Welfare, May 1996).

Example 1

Low-Caffeine Green Tea Extract A

A green tea extract ("POLYPHENON HG", product of Tokyo Food Techno Co., Ltd.; 200 g) was dispersed in a 95% aqueous ethanol solution (800 g) at room temperature under stirring at 250 r/min. After addition of acid clay "MIZUKA ACE #600" (product of Mizusawa Chemical Industries, Ltd.; 100 g), stirring was continued for about 10 minutes. Subsequently, filtration was conducted through No. 2 filter paper. Activated carbon (20 g) was then added, followed by filtration through No. 2 filter paper again. Re-filtration was then conducted through a 0.2-μm membrane filter. Finally, ion-exchanged water (200 g) was added to the filtrate, ethanol was distilled away at 40° C. and 0.0272 kg/cm², and the concentration of catechins was adjusted with ion-exchanged water to obtain a product.

Content of non-polymer catechins after the treatment: 22 wt %.
Non-polymer catechins/caffeine weight ratio after the treatment: 33.0
Gallates percentage after the treatment: 51 wt %.

Example 2

Low-caffeine Green Tea Extract B

A green tea extract ("POLYPHENON HG", product of Tokyo Food Techno Co., Ltd.; 100 g) was dispersed in a 70% aqueous ethanol solution (100 g) at room temperature under stirring at 250 r/min. After addition of activated carbon "KURARAY COAL GLC" (product of Kuraray Chemical K.K.; 25 g) and acid clay "MIZUKA ACE#600" (product of Mizusawa Chemical Industries, Ltd.; 30 g), stirring was continued for about 10 minutes. After a 95% aqueous ethanol solution (800 g) was added dropwise over 30 minutes, stirring was continued for 30 minutes at room temperature. Subsequently, filtration was conducted again through No. 2 filter paper. Re-filtration was then conducted through a 0.2-μm membrane filter. Finally, ion-exchanged water (200 g) was added to the filtrate, ethanol was distilled away at 40° C. and 0.0272 kg/cm², and the water content was adjusted to obtain a desired product.

Content of non-polymer catechins after the treatment: 22 wt %.
Non-polymer catechins/caffeine weight ratio after the treatment: 59.5
Gallates percentage after the treatment: 51.2 wt %.

Comparative Example 1

"POLYPHENON HG" (product of Tokyo Food Techno Co., Ltd.; 100 g) was dispersed as a green tea extract in water (900 g) at room temperature under stirring at 250 r/min. After the addition of acid clay "MIZUKA ACE #600" (product of Mizusawa Chemical Industries, Ltd.; 100 g), stirring was continued for about 20 minutes. Subsequently, stirring was continued for about 30 minutes at room temperature. After filtration was conducted through No. 2 filter paper, re-filtration was conducted through a 0.2-μm membrane filter. Finally, water was gradually evaporated by a drying apparatus until the concentration of non-polymer catechins became equivalent to that in Example 1 to obtain a product.

Content of non-polymer catechins after the treatment: 22 wt %.
Non-polymer catechins/caffeine weight ratio after the treatment: 23.6
Gallates percentage after the treatment: 49.6 wt %.

Comparative Example 2

"POLYPHENON HG" (product of Tokyo Food Techno Co., Ltd.; 100 g) was dispersed as a green tea extract in water (900 g) at room temperature under stirring at 250 r/min. After the addition of activated carbon "KURARAY COAL GLC" (product of Kuraray Chemical K.K.; 20 g) and acid clay "MIZUKA ACE #600" (product of Mizusawa Chemical Industries, Ltd.; 100 g), stirring was continued for about 20 minutes. Stirring was then continued for about 30 minutes at room temperature. After filtration was conducted through No. 2 filter paper, re-filtration was conducted through a 0.2-μm membrane filter. Finally, water was gradually evaporated by a drying apparatus until the concentration of non-polymer catechins became equivalent to that in Example 1 to obtain a product.

Content of non-polymer catechins after the treatment: 22 wt %.
Non-polymer catechins/caffeine weight ratio after the treatment: 42.6
Gallates percentage after the treatment: 47.6 wt %.

As shown in Table 1, the combined use of activated carbon and acid clay while employing an aqueous solution, which contains an organic solvent at a very high concentration, enables production of a purified green tea extract having good color and stability in which caffeine content is lowered without changing the gallates percentage and gallocatechins percentage of its non-polymer catechins.

TABLE 1

|  | Present invention | | Comparison | |
| --- | --- | --- | --- | --- |
|  | Example 1 | Example 2 | Comp. Ex. 1 | Comp. Ex. 2 |
| Solid green tea extract (g)[1] | 200 | 100 | 100 | 100 |
| Ethanol (g) | 760 | 830 | 0 | 0 |
| Water (g) | 40 | 70 | 900 | 900 |
| Activated carbon (g)[2] | 20 | 25 | 0 | 20 |
| Acid clay (g)[3] | 100 | 30 | 100 | 100 |
| Organic solvent/water (weight ratio) | 95/5 | 92/8 | 0/100 | 0/100 |
| Non-polymer catechins after treatment (wt %)[4] | 6.26 | 6.25 | 6.75 | 7.42 |
| GC | 29.71 | 29.72 | 31.75 | 34.72 |
| EGC | 2.00 | 1.92 | 2.22 | 2.02 |
| C | 9.92 | 10.01 | 9.64 | 8.24 |
| EC | 37.65 | 37.65 | 35.93 | 35.86 |
| EGCg | 1.26 | 1.23 | 1.39 | 1.47 |
| GCg | 12.14 | 12.19 | 11.34 | 9.61 |
| ECgC | 1.08 | 1.02 | 0.94 | 0.66 |

TABLE 1-continued

|  | Present invention | | Comparison | |
| --- | --- | --- | --- | --- |
|  | Example 1 | Example 2 | Comp. Ex. 1 | Comp. Ex. 2 |
| Non-polymer catechins/caffeine after treatment (weight ratio) | 33.0 | 59.5 | 23.6 | 42.6 |
| Gallates percentage of non-polymer catechins after treatment (wt %) | 51.0 | 51.2 | 49.6 | 47.6 |
| Gallocatechins percentage of non-polymer catechins after treatment (wt %) | 74.9 | 73.5 | 75.8 | 79.5 |
| Concentration of non-polymer catechins in solids after treatment (wt %) | 66 | 64 | 34 | 34 |
| Absorbance (−) | 0.038 | 0.031 | 0.535 | 0.270 |
| Assessment of purified products | Caffeine content was lowered, color was good, and stability was visually good. | Caffeine content was lowered, color was good, and stability was visually good. | Color deteriorated, and precipitation occurred. | Color deteriorated, and precipitation occurred. |

(Note) 1) "POLYPHENON HG", product of Tokyo Food Techno Co., Ltd.
2) "KURARAY COAL GLC", product of Kuraray Chemical K.K.
3) "MIZUKA ACE #600", product of Mizusawa Chemical Industries, Ltd.
4) Composition of non-polymer catechins in the "POLYPHENON HG" preparation:
   GC (gallocatechin) 6.39 wt %, EGC (epigallocatechin) 29.42 wt %, C (catechin) 2.16 wt %, EC (epicatechin) 10.3 wt %, EGCg (epigallocatechin gallate) 37.13 wt %, GCg (gallocatechin gallate) 1.93 wt %, ECg (epicatechin gallate) 11.89 wt %, Cg (catechin gallate) 0.79 wt %, gallates percentage 51.73 wt %, gallocatechins percentage 74.88 wt %

Example 3

Packaged Beverages

Formulated solutions were prepared by adding the respective green tea extracts shown in Table 1, adding the ingredients described in Table 2, and then bringing the total amounts to 100 with ion-exchanged water, respectively. The formulated solutions were subjected to a sterilization step according to the Food Sanitation Act and hot-pack filling to obtain packaged beverages.

The green tea extract C had the following composition:
Green Tea Extract C
Caffeine-containing catechin composition ("POLYPHENON HG", product of Tokyo Food Techno Co., Ltd).
Content of non-polymer catechins 33.70 wt %, caffeine content 5.5 wt %, non-polymer catechins/caffeine: 6.1, gallates percentage 51 wt %.

Five trained male assessors were used. Those assessors ingested 350 mL of each beverage, and assessed the beverages by giving ranking scores to their mouth refreshment shortly after drinking in accordance with the following standards.
5: Very good mouth refreshment
4: Good mouth refreshment
3: Slightly good mouth refreshment
2: Slightly poor mouth refreshment
1: Poor mouth refreshment

TABLE 2

|  | Invention products | | Comparative product |
| --- | --- | --- | --- |
| Formulations | 1 | 2 | 1 |
| Low-caffeine green tea extract A | 1.00 | — | — |
| Low-caffeine green tea extract B | — | 1.00 | — |
| Green tea extract C | — | — | 0.65 |
| Antioxidant | 0.03 | 0.03 | 0.03 |
| Sour seasoning | 0.30 | 0.30 | 0.30 |
| Sweetener | 5.00 | 5.00 | 5.00 |
| Fruit juice | 0.05 | 0.05 | 0.05 |
| Ion-exchanged water | Balance | Balance | Balance |
| Total amount | 100 | 100 | 100 |
| PH of beverage | 3.5 | 3.5 | 3.6 |
| Non-polymer catechins (wt %) | 0.22 | 0.22 | 0.22 |
| Non-polymer catechins/caffeine ratio | 33 | 59.5 | 6.1 |
| Mouth refreshment shortly after drinking | 4 | 5 | 1 |

As evident from the results of Table 2, a packaged beverage with outstanding mouth refreshment shortly after its drinking can be obtained by using a low-caffeine green tea extract in which, while maintaining the composition of catechins, caffeine has been selectively removed by treating a green tea extract in accordance with the present invention.

Example 4

In a similar manner as in Example 3, packaged beverages were produced by mixing the ingredients shown in Table 3 and conducting predetermined post-treatments.

It is to be noted that the green tea extract D was produced in accordance with the following process.
Green Tea Extract D
A caffeine-containing catechin composition ("POLYPHENON HG", product of Tokyo Food Techno Co., Ltd.; 100 g) was dispersed in a 95% aqueous ethanol solution (490.9 g) at room temperature under stirring at 250 r/min. After addition of activated carbon "KURARAY COAL GLC" (product of Kuraray Chemical K.K.; 25 g) and acid clay "MIZUKA ACE #600" (product of Mizusawa Chemical Industries, Ltd.; 30 g), stirring was continued for about 10 minutes. After a 40% aqueous ethanol solution (409.1 g) was added dropwise over 10 minutes, stirring was continued for about 30 minutes at room temperature. Subsequently, the activated carbon and precipitates were filtered out by No. 2 filter paper, and re-filtration was conducted through a 0.2-µm membrane filter. Finally, ion-exchanged water (200 g) was added to the filtrate, ethanol was distilled away at 40° C. and 0.0272 kg/cm$^2$, and the water content was adjusted to obtain the desired product.

Content of non-polymer catechins after the treatment: 22 wt %.

Non-polymer catechins/caffeine weight ratio after the treatment: 20.0

Gallates percentage after the treatment: 51 wt %.

An assessment was performed to determine whether or not the beverages according to the present invention are suited for long-term drinking. Using ten trained assessors, drinking of 500 mL per day was continued for 21 days to give a ranking score in accordance with the following standards.

A: Suited
B: Somewhat suited
C: A little hard to continue drinking
D: Not suited for long-term drinking Ten trained male assessors were used. Those assessors ingested 500 mL of each beverage, and assessed the beverages by giving ranking scores to their mouth refreshment shortly after drinking in accordance with the following standards.

A: Good mouth refreshment
B: Slightly good mouth refreshment
C: Slightly poor mouth refreshment
D: Poor mouth refreshment The assessment results are shown in Table 3.

% aqueous ethanol solution (800 g) at room temperature under stirring at 400 r/min, and the dispersion was stirred for about 10 minutes. A green tea extract ("POLYPHENON HG", product of Tokyo Food Techno Co., Ltd.; 200 g) was added thereto, and stirring was continued for about 3 hours at room temperature.

Filtration was then conducted through No. 2 filter paper. The filtrate was brought into contact with activated carbon "KURARAY COAL GLC" (product of Kuraray Chemical K.K.; 20 g), and re-filtration was then conducted through a 0.2-µm membrane filter. Finally, ion-exchanged water (200 g) was added to the filtrate, ethanol was distilled away at 40° C. and 0.0272 kg/cm$^2$, and the water content was adjusted to obtain a product.

Acid clay/non-polymer catechins weight ratio: 1.5
Post-treatment: non-polymer catechins/(free acids+proteins): 17

Example 6

Purified Green Tea Extract F

Acid clay "MIZUKA ACE#600" (product of Mizusawa Chemical Industries, Ltd.; 100 g) and citric acid (6.0 g) were dispersed in a 92.4 wt % aqueous ethanol solution (800 g) at room temperature under stirring at 400 r/min, and the dispersion was stirred for about 10 minutes. A green tea extract ("POLYPHENON HG", product of Tokyo Food Techno Co., Ltd.; 200 g) was added thereto, and stirring was continued for about 3 hours at room temperature.

TABLE 3

| Formulations | Invention products | | | Comparative products | | | |
| --- | --- | --- | --- | --- | --- | --- | --- |
| | 3 | 4 | 5 | 2 | 3 | 4 | 5 |
| Low-caffeine green tea extract A | 1.00 | 2.00 | 0.50 | 5.00 | 0.1 | — | — |
| Green tea extract C | — | — | — | — | — | — | 0.65 |
| Green tea extract D | — | — | — | — | — | 1.00 | — |
| Antioxidant | 0.03 | 0.03 | 0.03 | 0.03 | 0.03 | 0.03 | 0.03 |
| Sour seasoning | 0.30 | 0.30 | — | 0.30 | 0.30 | 0.30 | 0.30 |
| pH adjuster | — | — | — | — | — | — | — |
| Sweetener | 5.00 | 5.00 | — | 5.00 | 5.00 | 5.00 | 5.00 |
| Mineral salts (Na, K) | 0.07 | 0.07 | — | 0.07 | 0.07 | 0.07 | 0.07 |
| Fruit juice | 0.05 | 0.05 | — | 0.05 | 0.05 | 0.05 | 0.05 |
| Black tea flavor | — | — | 0.1 | — | — | — | — |
| Ion-exchanged water | Balance | Balance | Balance | Balance | Balance | Balance | Balance |
| Total amount | 100 | 100 | 100 | 100 | 100 | 100 | 100 |
| pH of beverage | 3.5 | 3.5 | 6.0 | 3.6 | 3.5 | 3.6 | 3.6 |
| Non-polymer catechins (wt %) | 0.22 | 0.44 | 0.11 | 1.10 | 0.02 | 0.2 | 0.22 |
| Non-polymer catechins/caffeine ratio | 33 | 33 | 33 | 33 | 33 | 22 | 6.1 |
| Long-term drinkability | A | A | B | D | A | C | D |
| Mouth refreshment shortly after drinking | A | A | A | C | A | C | D |

As evident from the results of Table 3, a packaged beverage suited for long-term drinking and capable of providing outstanding mouth refreshment shortly after its drinking can be obtained by using a low-caffeine green tea extract in which, while maintaining the composition of catechins, caffeine has been selectively removed by treating a green tea extract in accordance with the present invention.

Example 5

Purified Green Tea Extract E

Acid clay "MIZUKA ACE#600" (product of Mizusawa Chemical Industries, Ltd.; 100 g) was dispersed in a 92.4 wt Filtration was then conducted through No. 2 filter paper. The filtrate was brought into contact with activated carbon "KURARAY COAL GLC" (product of Kuraray Chemical K.K.; 20 g), and re-filtration was then conducted through a 0.2-µm membrane filter. Finally, ion-exchanged water (200 g) was added to the filtrate, ethanol was distilled away at 40° C. and 0.0272 kg/cm$^2$, and the water content was adjusted to obtain a product.

Citric acid/non-polymer catechins weight ratio: 0.08
Post-treatment: non-polymer catechins/(free acids+proteins): 18

Example 7

Purified Green Tea Extract G

Acid clay "MIZUKA ACE#600" (product of Mizusawa Chemical Industries, Ltd.; 100 g) was dispersed in a 92.4 wt % aqueous ethanol solution (800 g) at room temperature under stirring at 400 r/min, and the dispersion was stirred for about 10 minutes. A green tea extract ("POLYPHENON HG", product of Tokyo Food Techno Co., Ltd.; 200 g) was added thereto, and stirring was continued for about 3 hours at room temperature. After the temperature was raised to 40° C., stirring was continued for about 3 hours.

While maintaining the temperature at 40° C., filtration was conducted through No. 2 filter paper. The filtrate was then brought into contact at room temperature with activated carbon "KURARAY COAL GLC" (product of Kuraray Chemical K.K.; 20 g), and re-filtration was conducted through a 0.2-μm membrane filter. Finally, ion-exchanged water (200 g) was added to the filtrate, ethanol was distilled away at 40° C. and 0.0272 kg/cm², and the water content was adjusted to obtain a product.

Post-treatment: non-polymer catechins/(free acids+proteins): 20

Example 8

Purified Green Tea Extract H

Acid clay "MIZUKA ACE#600" (product of Mizusawa Chemical Industries, Ltd.; 100 g) and citric acid (6.0 g) were dispersed in a 92.4 wt % aqueous ethanol solution (800 g) at room temperature under stirring at 400 r/min, and the dispersion was stirred for about 10 minutes. A green tea extract ("POLYPHENON HG", product of Tokyo Food Techno Co., Ltd.; 200 g) was added thereto, and stirring was continued for about 3 hours at room temperature. After the temperature was raised to 40° C., stirring was continued for about 3 hours.

While maintaining the temperature at 40° C., filtration was conducted through No. 2 filter paper. The filtrate was then brought into contact at room temperature with activated carbon "KURARAY COAL GLC" (product of Kuraray Chemical K.K.; 20 g), and re-filtration was conducted through a 0.2-μm membrane filter. Finally, ion-exchanged water (200 g) was added to the filtrate, ethanol was distilled away at 40° C. and 0.0272 kg/cm², and the water content was adjusted to obtain a product.

Post-treatment: non-polymer catechins/(free acids+proteins): 19

Comparative Example 3

A green tea extract ("POLYPHENON HG", product of Tokyo Food Techno Co., Ltd.; 200 g) was dispersed in water (900 g) at room temperature under stirring at 250 r/min. After addition of activated carbon "KURARAY COAL GLC" (product of Kuraray Chemical K.K.; 40 g) and acid clay "MIZUKA ACE #600" (product of Mizusawa Chemical Industries, Ltd.; 200 g), stirring was continued for about 20 minutes. Subsequently, stirring was continued for 30 minutes at room temperature. After filtration was conducted through No. 2 filter paper, re-filtration was conducted through a 0.2-μm membrane filter. Finally, water was gradually evaporated by a drying apparatus until the concentration of non-polymer catechins became equivalent to that in Example 1 to obtain a product.

The production conditions and the analysis results of the obtained green tea extracts in Examples 5 to 8 and Comparative Example 3 are shown in Table 4.

TABLE 4

|  | Present invention | | | | Comparison |
| --- | --- | --- | --- | --- | --- |
|  | Example 5 | Example 6 | Example 7 | Example 8 | Comp. Ex. 3 |
| Solid green tea extract (g) | 200 | 200 | 200 | 200 | 200 |
| Ethanol (g) | 739.2 | 739.2 | 739.2 | 739.2 | 0 |
| Water (g) | 60.8 | 60.8 | 60.8 | 60.8 | 900 |
| Activated carbon (g) | 20 | 20 | 20 | 20 | 40 |
| Acid clay (g) | 100 | 100 | 100 | 100 | 200 |
| Organic acid (g) | 0 | 5.6 | 0 | 5.6 | 0 |
| Organic solvent/water (weight ratio) | 92/8 | 92/8 | 92/8 | 92/8 | 0/100 |
| Dissolution temperature (° C.) | 25 | 25 | 25→40 | 25→40 | 25 |
| pH of the mixture | 5.8 | 4.6 | 4.8 | 4.7 | 6.5 |
| Non-polymer catechins after treatment (wt %) |  |  |  |  |  |
| GC | 5.55 | 4.95 | 6.04 | 5.92 | 7.42 |
| EGC | 26.03 | 23.81 | 28.33 | 28.45 | 34.72 |
| C | 2.84 | 2.62 | 3.09 | 3.13 | 2.02 |
| EC | 8.49 | 7.45 | 9.24 | 8.90 | 8.24 |
| EGCg | 35.47 | 32.61 | 38.60 | 38.97 | 35.86 |
| GCg | 1.15 | 0.96 | 1.24 | 1.14 | 1.47 |
| ECg | 11.50 | 10.43 | 12.51 | 12.47 | 9.61 |
| Cg | 0.88 | 0.86 | 0.96 | 1.03 | 0.66 |
| Non-polymer catechins/caffeine (weight ratio) after treatment | 29.6 | 30.4 | 32.2 | 36.4 | 42.6 |
| Gallates percentage of non-polymer catechins after treatment (wt %) | 53.3 | 53.5 | 53.3 | 53.6 | 47.6 |
| Gallocatechins percentage of non-polymer catechins after treatment (wt %) | 74.3 | 74.8 | 74.2 | 74.5 | 79.5 |

TABLE 4-continued

|  | Present invention | | | | Comparison |
| --- | --- | --- | --- | --- | --- |
|  | Example 5 | Example 6 | Example 7 | Example 8 | Comp. Ex. 3 |
| Concentration of non-polymer catechins in solids after treatment (wt %) | 68 | 62 | 63 | 61 | 34 |
| Yield of non-polymer catechins (wt %) | 68 | 70 | 74 | 75 | 76 |
| Assessment of purified products | Caffeine content was lowered, color was good, and stability was visually good. | Caffeine content was lowered, color was good, and stability was visually good. | Caffeine content was lowered, color was good, and stability was visually good. | Caffeine content was lowered, color was rather good, and stability was visually good. | Color deteriorated, and precipitation occurred. |

\* Yield: Percentage of the amount of non-polymer catechins in a purified green tea extract based on the amount of non-polymer catechins in a green tea extract used as a feed material (wt %).
\* Composition of non-polymer catechins in the "POLYPHENON HG" preparation:
GC (gallocatechin) 6.39 wt %, EGC (epigallocatechin) 29.42 wt %, C (catechin) 2.16 wt %, EC (epicatechin) 10.3 wt %, EGCg (epigallocatechin gallate) 37.13 wt %, GCg (gallocatechin gallate) 1.93 wt %, ECg (epicatechin gallate) 11.89 wt %, Cg (catechin gallate) 0.79 wt %, gallates percentage 51.73 wt %, gallocatechins percentage 74.88 wt %

As shown in Table 4, use of acid clay and the contact treatment in a particular pH range while employing an aqueous solution which contains an organic solvent at a very high concentration enables production of a purified green tea extract having good color and stability in which caffeine content is lowered without changing the gallates percentage and gallocatechins percentage of the non-polymer catechins.

Example 9

Formulated solutions were prepared by adding the respective purified green tea extracts shown in Table 4 and then bringing the total amounts to 100 with ion-exchanged water, respectively. The formulated solutions were subjected to a sterilization step according to the Food Sanitation Act and hot-pack filling to obtain packaged beverages.

Five trained male assessors were used. Those assessors ingested 350 mL of each beverage, and assessed the beverages by giving ranking scores to their mouth refreshment shortly after drinking in accordance with the following standards.
5: Very good mouth refreshment
4: Good mouth refreshment
3: Slightly good mouth refreshment
2: Slightly poor mouth refreshment
1: Poor mouth refreshment As evident from the results of Table 5, a packaged beverage with outstanding mouth refreshment shortly after its drinking can be obtained by using an invention product in which, while maintaining the composition of catechins, caffeine has been selectively removed by treating a green tea extract in accordance with the present invention.

Example 10

Low-Caffeine Green Tea Extract I

Green tea leaves (steamed tea leaves from Sri Lanka; 100 g) were evenly mixed with an 80% aqueous ethanol solution (36.5 g), and were moistened at 5° C. for 15 hours. The moistened green tea leaves were charged in a semi-batch supercritical carbon dioxide extraction apparatus, and were treated with carbon dioxide which contained 2% of an 80% aqueous ethanol solution, at 30 MPa and 70° C. for 6 hours. The amount of carbon dioxide used for the treatment was 14 kg. Subsequent to the treatment, the extraction residue was dried under reduced pressure at 40° C. to obtain supercritical $CO_2$-treated green tea leaves (92 g). The green tea leaves were extracted at 92° C. for 1 hour with ion-exchanged water (10 L), followed by filtration to obtain an extract. The extract was lyophilized to obtain a green tea extract (40 g). The contents of non-polymer catechins and caffeine in the extract were 48

TABLE 5

|  | Invention products | | | | Comparative product |
| --- | --- | --- | --- | --- | --- |
| Formulations | 6 | 7 | 8 | 9 | 6 |
| Green tea extract (E) | 1.00 | | | | |
| Green tea extract (F) | | 1.00 | | | |
| Green tea extract (G) | | | 1.00 | | |
| Green tea extract (H) | | | | 1.00 | |
| Extract of Comparative Example 3 | | | | | 1.00 |
| Antioxidant | 0.03 | 0.03 | 0.03 | 0.03 | 0.03 |
| Sour seasoning | 0.30 | 0.30 | 0.30 | 0.30 | 0.30 |
| Sweetener | 5.00 | 5.00 | 5.00 | 5.00 | 5.00 |
| Fruit juice | 0.05 | 0.05 | 0.05 | 0.05 | 0.05 |
| Ion-exchanged water | Balance | Balance | Balance | Balance | Balance |
| Total amount | 100 | 100 | 100 | 100 | 100 |
| pH of beverage | 3.5 | 3.4 | 3.5 | 3.5 | 3.6 |
| Non-polymer catechins (wt %) | 0.22 | 0.22 | 0.22 | 0.22 | 0.22 |
| Non-polymer catechins/caffeine | 29.6 | 30.4 | 32.2 | 36.4 | 42.6 |
| Mouth refreshment shortly after drinking | 4 | 3 | 4 | 3 | 1 | wt % and 2.2 wt %, respectively, and the non-polymer catechins/caffeine weight ratio was 22.

The thus-obtained green tea extract (20 g) was suspended in a 95% aqueous ethanol solution (98.18 g) at room temperature under stirring at 250 r/min. After addition of activated carbon ("KURARAY COAL GLC", product of Kuraray Chemical K.K.; 4 g) and acid clay ("MIZUKA ACE #600", product of Mizusawa Chemical Industries, Ltd.; 20 g), stirring was continued for about 10 minutes. After a 40% aqueous ethanol solution (82 g) was added dropwise over 10 minutes, stirring was continued for 40 minutes at room temperature. After the activated carbon and precipitates were filtered out by No. 2 filter paper, re-filtration was conducted through a 0.2-μm membrane filter. Finally, ion-exchanged water (40 g) was added to the filtrate, and ethanol was distilled away at 40° C. and $3.4 \times 10^{-3}$ MPa to obtain a product. The contents of non-polymer catechins and caffeine in the product were 263 mg/100 mL and 4.3 mg/100 mL, respectively, and the non-polymer catechins/caffeine weight ratio was 61.

TABLE 6

|  |  | Example 10 |
|---|---|---|
| Moistening step of green tea leaves | Charged amount of green tea leaves (g) | 100 |
|  | Moistening solvent | 80% aq. soln. of ethanol |
|  | Amount of moistening solvent | 36.5 |
| Supercritical carbon dioxide treatment step | Extraction pressure (MPa) | 30 |
|  | Extraction temperature (° C.) | 70 |
|  | Extraction time (h) | 6 |
|  | Added solvent | 80% aq. soln. of ethanol |
|  | Amount of added solvent (wt %) | 2 |
|  | Amount of tea leaves recovered after treatment (g) | 92 |
| Extraction step for green tea extract | Extraction solvent | Ion-exchanged water |
|  | Amount of extraction solvent (L) | 10 |
|  | Amount of extract (g) | 40 |

Example 11

Using the tea extract obtained in Example 10, the citrus-flavored, packaged beverage described in Table 7 was produced. The thus-obtained beverage was taken by eight trained male assessors, and was assessed for the following five features. The results are shown in Table 7.

Assessed Features

| Tea flavor and taste (5-stage assessment): | |
|---|---|
| 1 | Weak |
| 2 | Slightly weak |
| 3 | Average |
| 4 | Slightly strong |
| 5 | Strong |
| Citrus flavor and taste (5-stage assessment): | |
| 1 | Weak |
| 2 | Slightly weak |
| 3 | Average |
| 4 | Slightly strong |
| 5 | Strong |
| Taste assessment (5-stage assessment): | |
| 1 | Unpalatable |
| 2 | Slightly unpalatable |
| 3 | Average |
| 4 | Slightly tasty |
| 5 | Tasty |
| Changes in flavor and taste during high-temperature storage (3-stage assessment): | |
| A | Not changed |
| B | Slightly changed |
| C | Changed |

TABLE 7

|  | Added ingredients | Invention product 10 |
|---|---|---|
| Beverage formulation | Supercritically treated product*[1] | 460 |
|  | Artificial sweetener*[2] | 8 |
|  | Sour seasoning | 2.1 |
|  | Ascorbic acid | 0.3 |
|  | NaCl | 0.6 |
|  | KCl | 0.4 |
|  | Dextrins | 5 |
|  | Citrus fruit juice[3] | 2 |
|  | Citrus flavor[4] | 5.5 |
|  | Ion-exchanged water | Balance |
|  | Total | 1000 |
|  | Non-polymer catechins in beverage (wt %) | 0.12 |
|  | Non-polymer catechins/caffeine ratio in beverage (−) | 61 |
| Assessment results | Tea flavor and taste | 1 |
|  | Citrus flavor and taste | 5 |
|  | Taste assessment | 5 |
|  | Changes in flavor and taste during high-temperature storage (product stored at 37° C. for 3 months) | A |

*[1] Green tea extract of Example 10
*[2] Sucralose
*3 Grape fruit
*4 Grape fruit It is appreciated from Table 7 that the packaged beverage according to the present invention, which used the low-caffeine green tea extract purified using the extract from the tea leaves as the supercritical extraction residue, was extremely reduced in tea flavor and taste, exhibited the flavor and taste of the added citrus fruit juice and flavor, did not exhibit a green tea-derived flavor and taste which would have been otherwise developed after high-temperature storage, and was inhibited from flavor and taste changes.

The invention claimed is:

1. A process for production of a low-caffeine green tea extract containing from 25 to 90 wt % of non-polymer catechins based on a dry weight of said extract, which comprises bringing a green tea extract, a mixture comprising ethanol and water in a weight ratio of ethanol/water of 91/9 to 97/3, activated carbon, and 2.5 to 25 weight parts of acid clay or activated clay based on 100 weight parts of said mixture of ethanol and water into contact with one another,
   wherein a weight ratio of activated carbon to acid clay or activated clay is from 1 to 10 parts of acid clay or activated clay to 1 part of activated carbon.

2. The process according to claim 1, wherein the green tea extract is dissolved in said mixture of the ethanol and water and is then brought into contact with activated carbon and acid clay or activated clay.

3. The process according to claim 1, wherein the green tea extract is brought into contact with acid clay or activated clay and then with activated carbon.

4. The production process according to any one of claim 1, 2 or 3, wherein the green tea extract used as a raw material is a tea extract extracted from leaves of the genus *Camellia* which have been treated to contact with carbon dioxide in a supercritical state.

5. The process according to claim 1, 2 or 3, wherein the weight ratio of the non-polymer catechins to caffeine in the low-caffeine green tea extract is from 25 to 200.

6. A process for selectively removing caffeine from a caffeine-containing catechin composition, which comprises dispersing a green tea extract in a mixture comprising ethanol and water in a weight ratio of ethanol/water of 91/9 to 97/3 and bringing the resulting dispersion into contact with activated carbon and 2.5 to 25 weight parts of acid clay or activated clay based on 100 weight parts of said mixture of ethanol and water, wherein a weight ratio of activated carbon to acid clay or activated clay is from 1 to 10 parts of acid clay or activated clay to 1 part of activated carbon.

7. The process according to claim 3, wherein the acid clay is used in such an amount that the weight ratio of the acid clay to the non-polymer catechins (acid clay/non-polymer catechins) ranges from 0.9 to 5.0.

8. The process for production of a low-caffeine green tea extract according to claim 1, wherein said activated carbon has a pore volume of 0.01 to 0.8 mL/g.

9. The process for production of a low-caffeine green tea extract according to claim 1, wherein said acid clay or said activated clay has a specific surface area of from 50 to 350 $m^2/g$.

10. The process for production of a low-caffeine green tea extract according to claim 1, wherein a weight ratio of activated carbon: acid clay or activated clay is from 1:1 to 1:6.

* * * * *